United States Patent
Ikeda et al.

(10) Patent No.: US 7,519,448 B2
(45) Date of Patent: Apr. 14, 2009

(54) METHOD FOR DETERMINING POSITION OF SEMICONDUCTOR WAFER, AND APPARATUS USING THE SAME

(75) Inventors: Satoshi Ikeda, Mie-ken (JP); Masayuki Yamamoto, Osaka (JP)

(73) Assignee: Nitto Denko Corporation, Osaka (JP)

( * ) Notice: Subject to any disclaimer, the term of this patent is extended or adjusted under 35 U.S.C. 154(b) by 234 days.

(21) Appl. No.: 11/604,355

(22) Filed: Nov. 27, 2006

(65) Prior Publication Data

US 2007/0139642 A1 Jun. 21, 2007

(30) Foreign Application Priority Data

Dec. 2, 2005 (JP) ............... 2005-349076

(51) Int. Cl.
*G06F 19/00* (2006.01)
*G05B 19/18* (2006.01)
*G06K 9/00* (2006.01)

(52) U.S. Cl. .................. 700/114; 700/58; 700/59; 700/61; 700/121; 451/11; 451/914; 382/151; 702/95

(58) Field of Classification Search ............. 700/56–59, 700/61, 62, 66, 112, 114, 121, 178, 192, 700/194; 451/5, 6, 9–11, 914; 382/151; 702/94, 95, 150–153
See application file for complete search history.

(56) References Cited

U.S. PATENT DOCUMENTS

| 4,765,793 A | * | 8/1988 | Goddeau | 414/416.01 |
| 2005/0251279 A1 | * | 11/2005 | Ray | 700/114 |
| 2006/0222236 A1 | * | 10/2006 | Osada et al. | 382/151 |

FOREIGN PATENT DOCUMENTS

JP 08-279547 10/1996

* cited by examiner

*Primary Examiner*—Sean P. Shechtman
(74) *Attorney, Agent, or Firm*—Cheng Law Group PLLC

(57) ABSTRACT

A light source emits light toward a semiconductor wafer, and a light receiving sensor detects light passing a peripheral edge of the semiconductor wafer. Each coordinates of the peripheral edge of the semiconductor wafer is obtained from a result of the detection. Further, a center of the semiconductor wafer is obtained from a group of the coordinates. Then, an illumination device emits light toward the peripheral edge of the semiconductor wafer and an optical camera detects light reflected from the peripheral edge of the semiconductor wafer. A position of a "V"-shaped notch formed on the peripheral edge of the semiconductor wafer is obtained from a result of the detection. A handling position of the semiconductor wafer is determined based on the center of the semiconductor wafer and the position of the "V"-shaped notch.

18 Claims, 7 Drawing Sheets

METHOD FOR DETERMINING POSITION OF SEMICONDUCTOR WAFER, AND APPARATUS USING THE SAME

BACKGROUND OF THE INVENTION (1) Field of the Invention

The present invention relates to a method for detecting a detection site such as a notch or an orientation flat formed on a peripheral edge of a semiconductor wafer having a protective sheet joined thereto, thereby determining a handling position of the semiconductor wafer, and an apparatus using this method.

(2) Description of the Related Art

A semiconductor wafer (hereinafter, simply referred to as "wafer") has a bottom face subjected to processing by a mechanical method such as grinding or polishing, a chemical method such as etching, and the like. Thus, the wafer is reduced in thickness. Upon performance of the processing for the wafer by these methods, a protective sheet is joined to a top face of the wafer in order to protect a wiring pattern formed on the top face of the wafer. Then, the wafer having the protective sheet joined thereto is subjected to polishing. Thereafter, when the wafer is allowed to rotate and passes between a light source and a light receiving sensor provided so as to be opposite to each other with a peripheral edge of the wafer interposed therebetween, scanning is performed on the wafer; thus, positional information about the peripheral edge is acquired. A center of the wafer is obtained from this positional information.

The center of the wafer is obtained and, concurrently, positional information about a detection site such as a notch or an orientation flat to be used for alignment is obtained. A handling position of the wafer is determined based on this positional information. More specifically, the position of the detection site is used as a reference for determination of a handling position of the wafer upon transport or determination of a handling position in consideration of a rotational direction about a center axis of the wafer when a ring-shaped frame holds the bottom face of the wafer through adhesion of a support adhesive tape (refer to, for example, JP-A 08-279547).

However, a conventional method has the following problems.

In recent years, a wafer is reduced in thickness by grinding in such a manner that an almost circular protective sheet is joined to a top face of the wafer and, then, a coating film is formed on a ground bottom face by metal deposition or the like. Herein, the protective sheet on a notch formed on the wafer is bared; therefore, the coating film is disadvantageously attached to the bared portion of the protective sheet. Further, the deposited metal is uplifted at the peripheral edge of the wafer by surface tension.

Consequently, even when the peripheral edge of the wafer is irradiated with light, transmission of the light is hindered by the coating film at the notch. Hence, the light receiving sensor, provided so as to be opposite to the light source with the wafer interposed therebetween, fails to detect the light from the light source with good accuracy, so that the position of the notch cannot be obtained.

In addition, if the bottom face of the wafer is irradiated with light and the position of the notch is detected based on intensity of the light reflected from the bottom face, scattered reflection occurs due to the metal uplifted at the peripheral edge of the wafer. Consequently, only the position of the notch cannot be identified with good accuracy.

SUMMARY OF THE INVENTION

The present invention is made in view of the aforementioned circumstances. A principal object of the present invention is to provide a method for obtaining a position of a detection site formed on a peripheral edge of a semiconductor wafer, having a protective sheet joined thereto, with good accuracy, thereby determining a handling position of the semiconductor wafer with good accuracy, and an apparatus using this method.

In order to accomplish the aforementioned object, the present invention adopts the following configuration.

A method for detecting a detection site for alignment formed on a peripheral edge of a semiconductor wafer having a protective sheet joined thereto, thereby determining a handling position of the semiconductor wafer, the method comprising:

a first irradiation step of irradiating the peripheral edge of the semiconductor wafer having the protective sheet joined thereto with light from a light source;

a light receiving step of detecting the light from the light source through first detection means provided so as to be opposite to the light source with the semiconductor wafer interposed therebetween in a state that the peripheral edge of the semiconductor wafer is irradiated with the light from the light source;

a center determination step of determining a center of the semiconductor wafer based on a result of the detection by the first detection means;

a second irradiation step of irradiating the peripheral edge of the semiconductor wafer with light from a light source;

a reflection light detection step of detecting light reflected from the semiconductor wafer through second detection means in a state that the peripheral edge of the semiconductor wafer is irradiated with the light from the light source; and a detection site determination step of determining a position of the detection site based on a variation in intensity of the reflection light detected by the second detection means.

With the method according to the present invention, the first detection means provided so as to be opposite to the light source with the semiconductor wafer interposed therebetween can detect the light passing along the peripheral edge of the semiconductor wafer. For example, even in a case that the peripheral edge of the semiconductor wafer is coated with a coating film, the first detection means can detect the light passing along the peripheral edge of the semiconductor wafer without incurring an adverse influence of the coating film. Accordingly, positional information about an outer peripheral end of the semiconductor wafer can be obtained from the position of the light detected by the first detection means. Further, a center of the semiconductor wafer can be obtained from the positional information.

In addition, the light reflected from the peripheral edge of the semiconductor wafer varies in accordance with a status of a reflection face. More specifically, at the detection site having a reflection face different in status from that of the peripheral edge other than the detection site, intensity of light to be detected by the second detection means varies. Accordingly, the position of the detection site can be obtained from the variation in intensity of the light.

That is, even when the semiconductor wafer is coated with a coating film or the like, both the center of the semiconductor wafer and the position of the detection site can be obtained with good accuracy. Therefore, the handling position of the semiconductor wafer can be determined with good accuracy.

In the light receiving step and the reflection light detection step, preferably, a pair of the light source and the first detection means and the semiconductor wafer are allowed to move relatively in such a manner that the pair of the light source and the first detection means rotates about a center axis of the semiconductor wafer.

Preferably, the apparatus according to the present invention is configured as follows.

For example, the detection site formed on the peripheral edge of the semiconductor wafer is a notch.

In the center determination step, for example, the center of the semiconductor wafer is obtained by:

subjecting, to coordinate transformation, the position of the light detected by the first detection means along the peripheral edge of the semiconductor wafer;

calculating a distance between coordinates of a point optionally determined on a plane of the semiconductor wafer and each coordinates of the peripheral edge of the semiconductor wafer; and determining center coordinates based on a variation amount of a collection of the obtained distance data.

For example, the second detection means used in the detection site determination step is image capturing means such as a CCD camera.

In the detection site determination step, for example, the position of the notch formed on the peripheral edge of the semiconductor wafer is determined by:

capturing, through the image capturing means, an image of the peripheral edge of the semiconductor wafer irradiated with the light from the light source; and comparing predetermined reference image data of the notch with actual image data obtained by the image capturing means.

With the method according to the present invention, the position of the light detected by the first detection means is subjected to coordinate transformation; thus, a collection of coordinate data of an outer peripheral end of the semiconductor wafer can be acquired. Further, a distance from optional coordinates can be obtained for each coordinates of the outer peripheral end of the semiconductor wafer by means of coordinates of a point optionally determined on the plane of the semiconductor wafer and a collection of the previously obtained coordinate data. The center coordinates of the semiconductor wafer can be determined by a variation amount of the obtained distance data.

When the peripheral edge of the semiconductor wafer is irradiated with light, the image capturing means receives the light reflected from the peripheral edge other than the notch and the light reflected from the notch. That is, in the semiconductor wafer, the notch is different from the peripheral edge other than the notch with respect to intensity of reflection light received by the image capturing means. Therefore, actual image data can be obtained from the difference. By comparison between the actual image data and the predetermined reference image data of the notch, a correspondence position in shape can be obtained. Thus, the position of the notch formed on the peripheral edge of the semiconductor wafer can be determined.

Preferably, the position of the notch is determined by pattern matching between the reference image data and the actual image data.

In addition, a bottom face of the semiconductor wafer having the protective sheet joined thereto and a rear face of the protective sheet bared at the notch may be coated with a coating film for hindering transmission of light.

Herein, even when the bottom face of the semiconductor wafer and the rear face of the protective sheet bared at the notch are coated with the coating film for hindering transmission of light, the first detection means can detect the light passing along the peripheral edge of the semiconductor wafer with good accuracy. In addition, even when the protective sheet is coated with the coating film, a reflection face thereof is different in status from that of the semiconductor wafer. Accordingly, intensity of the reflection light varies, so that the position of the detection site can be obtained with good accuracy based on this variation.

In a case of the semiconductor wafer coated with the coating film, preferably, the second detection means detects the reflection light in a state that one of a white sheet and a white plate is provided so as to be opposite to the light source with the semiconductor wafer interposed therebetween.

With the method according to the present invention, when the white sheet or the white plate is provided so as to be opposite to the light source with the semiconductor wafer interposed therebetween, the peripheral edge of the semiconductor wafer can be emphasized by the light reflected by the white face.

In a case of using the method according to the present invention, preferably, the light source is a light source different from the light source provided so as to be opposite to the first detection means, is disposed on a side of the second detection means, and changes an angle of the light to be emitted to the semiconductor wafer.

In order to accomplish the aforementioned object, the present invention also adopts the following configuration.

An apparatus for detecting a detection site for alignment formed on a peripheral edge of a semiconductor wafer having a protective sheet joined thereto, thereby determining a handling position of the semiconductor wafer, the apparatus comprising:

holding means for holding the semiconductor wafer having the protective sheet joined thereto;

a light source for irradiating, with light, the peripheral edge of the semiconductor wafer held by the holding means;

first detection means, provided so as to be opposite to the light source with the semiconductor wafer interposed therebetween, for detecting a position of the light emitted from the light source;

rotational movement means for allowing a pair of the light source and the first detection means and the holding means to move relatively in such a manner that the pair of the light source and the first detection means moves along the peripheral edge of the semiconductor wafer held by the holding means;

second detection means for detecting light reflected from the semiconductor wafer among the light emitted from the light source toward the peripheral edge of the semiconductor wafer;

computation means for obtaining a center of the semiconductor wafer based on the light detected by the first detection means and obtaining a position of the detection site based on a variation in intensity of the reflection light detected by the second detection means in a state that the rotational movement means allows a pair of the light source and light receiving means and the holding means to move relatively; and control means for controlling the rotational movement means so as to perform alignment of the handling position of the semiconductor wafer held by the holding means in accordance with a result of the computations by the computation means.

With this configuration, the pair of the light source and the first detection means provided so as to be opposite to each other with the semiconductor wafer interposed therebetween and the holding means are allowed to move relatively in such a manner that the pair of the light source and the first detection means moves along the peripheral edge of the semiconductor wafer. At this movement, the first detection means can detect the light passing along the peripheral edge of the semiconductor wafer. Also at this movement, the second detection means can detect the light reflected from the peripheral edge of the semiconductor wafer.

Accordingly, the computation means obtains the center of the semiconductor wafer from the position of the light detected by the first detection means. Thus, the computation means can obtain the position of the detection site from the variation in intensity of the reflection light detected by the second detection means. Based on the center of the semiconductor wafer and the position of the detection site each obtained by the computation means, the control means controls the rotational movement means to thereby allow the semiconductor wafer to move toward an optional handling position.

With this configuration, it is possible to obtain the center of the semiconductor wafer and the position of the detection site with good accuracy. Thus, the apparatus according to the present invention can be realized suitably.

For example, the detection site formed on the peripheral edge of the semiconductor wafer is a notch.

In addition, the second detection means used upon determination of the detection site is image capturing means such as a CCD camera.

The computation means obtains the center of the semiconductor wafer by:

subjecting, to coordinate transformation, the position of the light detected by the first detection means along the peripheral edge of the semiconductor wafer;

calculating a distance between coordinates of a point optionally determined on a plane of the semiconductor wafer and each coordinates of the peripheral edge of the semiconductor wafer; and determining center coordinates based on a variation amount of a collection of the obtained distance data.

The computation means obtains the position of the notch formed on the peripheral edge of the semiconductor wafer by:

capturing, through the image capturing means, an image of the peripheral edge of the semiconductor wafer irradiated with the light from the light source; and comparing predetermined reference image data of the notch with actual image data obtained by the image capturing means.

Preferably, the computation means determines the position of the notch by pattern matching between the reference image data and the actual image data.

In the apparatus according to the present invention, preferably, the light source includes: a first light source provided so as to be opposite to the first detection means with the semiconductor wafer interposed therebetween; and a second light source for irradiating the peripheral edge of the semiconductor wafer with light, and one of a white sheet and a white plate is provided so as to be opposite to the second light source with the semiconductor wafer interposed therebetween.

With this configuration, parameters such as an output and an emission angle of each light source can be adjusted optionally. Further, when the white sheet or the white plate is provided so as to be opposite to the light source with the semiconductor wafer interposed therebetween, the peripheral edge of the semiconductor wafer can be emphasized by the light reflected by the white face.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

DESCRIPTION OF THE PREFERRED EMBODIMENT

Hereinafter, description will be given of an apparatus for determining a position of a semiconductor wafer according to an embodiment of the present invention with reference to the drawings. This apparatus can implement a method according to the present invention.

Figure 1:
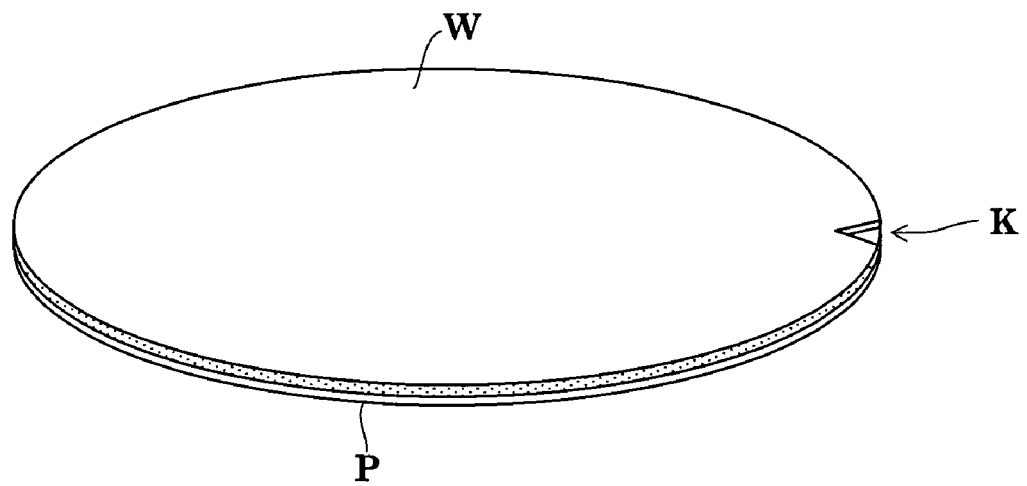
FIG. 1 is a perspective view schematically illustrating a configuration of a semiconductor wafer used in an embodiment of the present invention.
Figure 2:
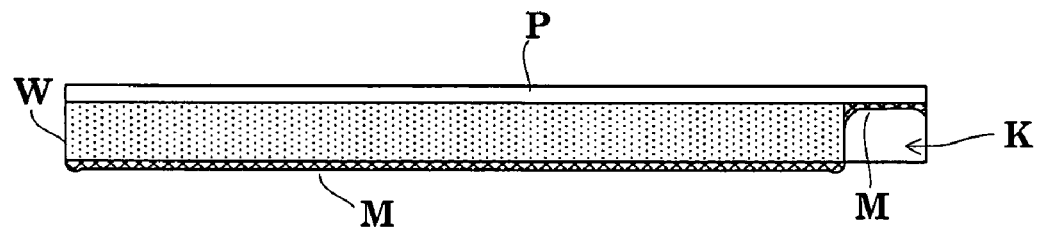
FIG. 2 is a sectional view of a semiconductor wafer.

As illustrated in FIG. 1, to a semiconductor wafer (hereinafter, simply referred to as "wafer") W used in the embodiment, an almost circular protective sheet P is joined so as to protect a circuit pattern formed a top face of the wafer W. In this state, further, the wafer W is reduced in thickness by grinding of a bottom face thereof. Thereafter, metal M is deposited on the bottom face of the wafer W. Of course, the metal M is deposited on a rear face of the protective sheet P bared at a "V"-shaped notch K which is a detection site formed on the wafer W and used for determining a handling position of the wafer W. Further, as illustrated in FIG. 2, the deposited metal M is uplifted by its surface tension at a peripheral edge of the wafer W. Hereinafter, description will be given of a specific configuration of the apparatus according to the embodiment of the present invention. It is to be noted that the "V"-shaped notch K corresponds to a notch in the present invention.

Figure 3:
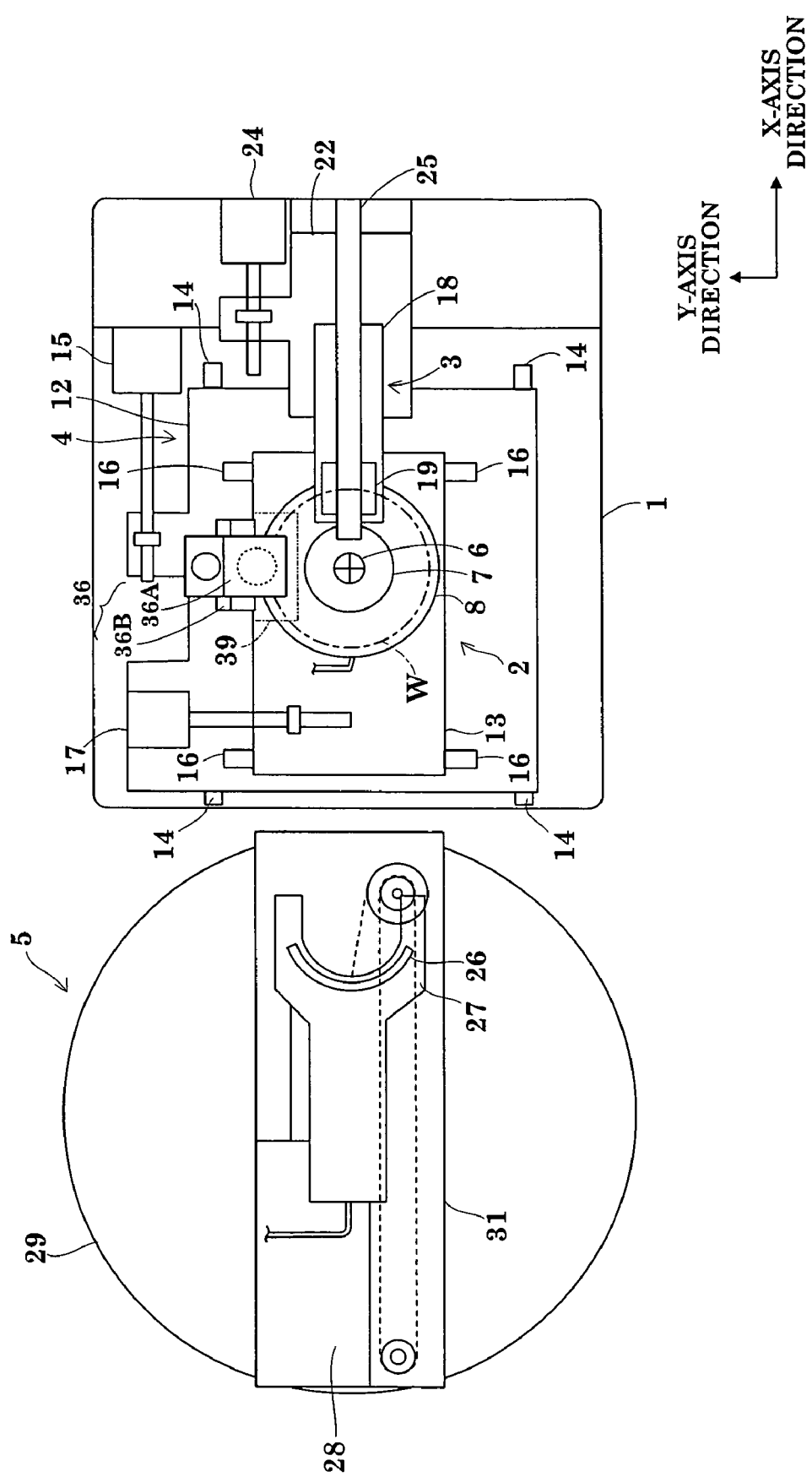
FIG. 3 is a plan view schematically illustrating a general configuration of an apparatus for determining a position of a semiconductor wafer according to the embodiment of the present invention.
Figure 4:
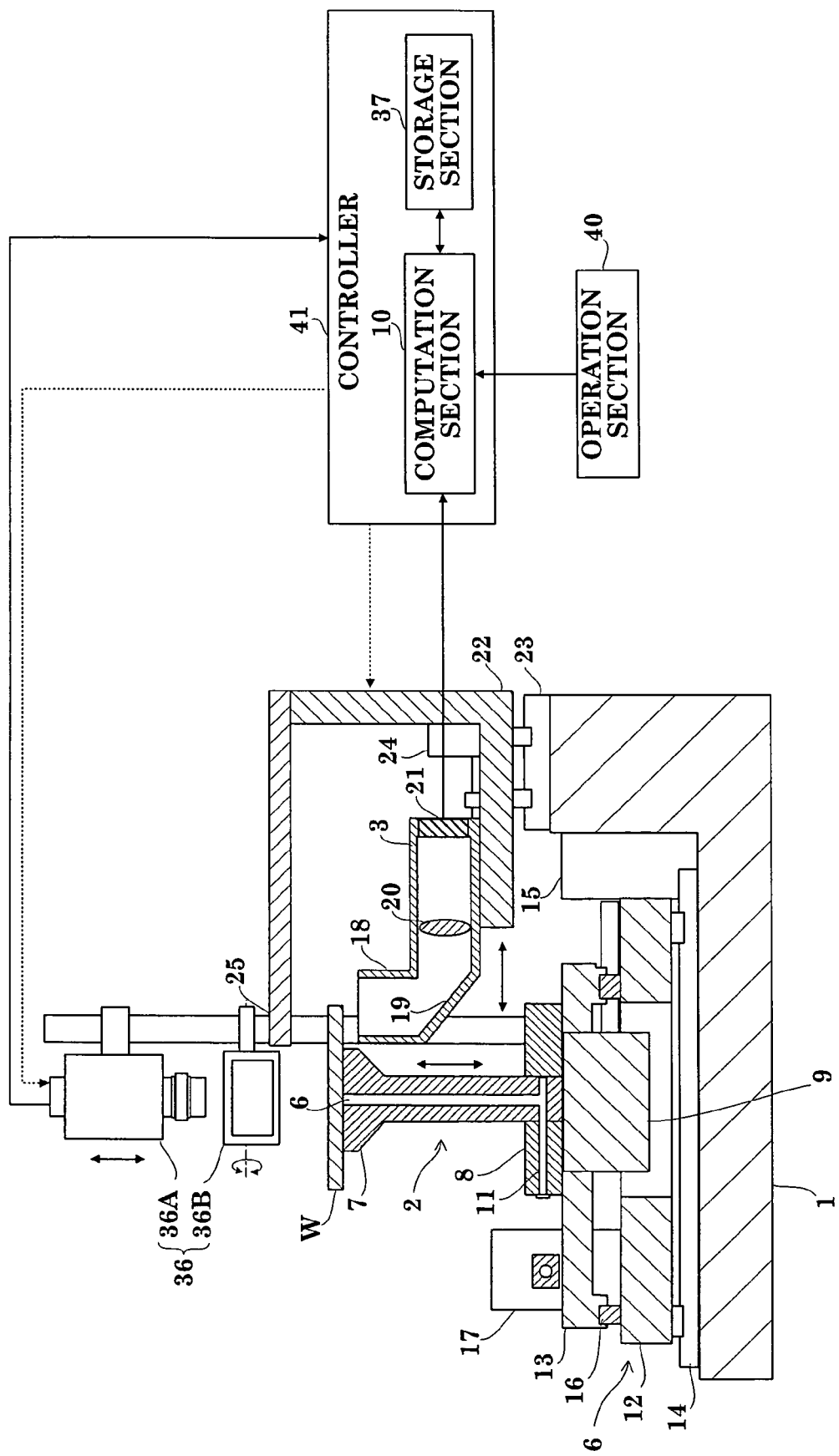
FIG. 4 is a side view illustrating a main configuration of the apparatus according to the embodiment of the present invention.

FIG. 3 is a plan view illustrating the apparatus according to the embodiment of the present invention. FIG. 4 is a side view illustrating a main configuration of the apparatus according to the embodiment of the present invention.

As illustrated in FIGS. 3 and 4, the apparatus according to the embodiment of the present invention comprises a rotation mechanism 2, a first peripheral edge measurement mechanism 3, a second peripheral edge measurement mechanism 36, a computation section 10 (not illustrated), a vertical drive mechanism 4 and a transport mechanism 5. Herein, the rotation mechanism 2 allows the wafer W to rotate while holding the bottom face of the wafer W in such a posture that the pattern face of the wafer W, having the protective sheet P joined thereto, is directed upward. Each of the first peripheral edge measurement mechanism 3 and the second peripheral edge measurement mechanism 36 measures the peripheral edge of the wafer W held by the rotation mechanism 2. The computation section 10 collects an rotational angle of the rotation mechanism 2 and positional data of the peripheral edge of the wafer W corresponding to the rotational angle in order to perform a predetermined computation. The vertical drive mechanism 4 allows the rotation mechanism 2 to move in a vertical direction with respect to a rotational axis. The transport mechanism 5 transmits/receives the wafer W to/from the rotation mechanism 2.

It is to be noted that the rotation mechanism 2 corresponds to rotational movement means in the present invention.

The rotation mechanism 2 includes a cylindrical holding stage 7 sucking the bottom face of the wafer W through a suction hole 6 formed on a top face thereof, and a stage pedestal 8 rotatably supporting the holding stage 7. It is to be noted that the holding stage 7 corresponds to holding means in the present invention.

A pulse motor 9 for rotation is consecutively provided at a lower portion of the holding stage 7. When the pulse motor 9 for rotation is driven, the rotation mechanism 2 is rotatable. Herein, the pulse motor 9 for rotation is fixed to the vertical drive mechanism 4. The pulse motor 9 for rotation sends a digital signal to the computation section 10 (to be described later) at each certain rotational angle. Herein, the certain rotational angle may be, for example, 0.036°. When the rotation mechanism 2 rotates once, the pulse motor 9 for rotation sends a digital signal of 1000 pulses to the computation section 10 of a controller 41. A suction device (not illustrated) is communicated with the suction hole 6 via a hole 11 of the stage pedestal 8. That is, the suction device gives a suction force for sucking the wafer W to the suction hole 6.

The vertical drive mechanism 4 includes an X-axis stage 12 slidable in an X-axis direction illustrated in FIG. 3, and a Y-axis stage 13 movable in a Y-axis direction illustrated in FIG. 3. The X-axis stage 12 is mounted on an X-axis linear guide 14 laid on a base 1 of the apparatus according to the embodiment of the present invention. When an X-axis pulse motor 15 fixed to the base 1 is driven, the X-axis stage 12 is movable in the X-axis direction.

On the other hand, the Y-axis stage 13 is mounted on a Y-axis linear guide 16 laid on the X-axis stage 12. When a Y-axis pulse motor 17 fixed to the X-axis stage 12 is driven, the Y-axis stage 13 is movable in the Y-axis direction. Each of the stage pedestal 8 and the pulse motor 9 for rotation is fixed to the Y-axis stage 13.

The first peripheral edge measurement mechanism 3 is provided beside the holding stage 7. The first peripheral edge measurement mechanism 3 includes an almost "L"-shaped cylindrical body 18, a mirror 19 provided in the cylindrical body 18, a lens 20, and a light receiving sensor 21. It is to be noted that the light receiving sensor 21 corresponds to first detection means in the present invention.

The mirror 19 is provided at a bent portion of the almost "L"-shaped cylindrical body 18, and is fixed in a slanting direction at an angle of 45° when viewed from front in FIG. 4 in order to direct light entering from an upper opening of the cylindrical body 18 toward the light receiving sensor 21 located rightward in FIG. 4.

The light receiving sensor 21 is fixed to a longitudinal end of the cylindrical body 18 at a position beside the mirror 19.

The lens 20 is fixedly provided between the mirror 19 and the light receiving sensor 21 in the cylindrical body 18 so as to converge the light reflected from the mirror 19 onto the light receiving sensor 21. Herein, the light receiving sensor 21 is a one-dimensional line sensor having a plurality of light receiving elements arranged in a line, and sends light reception data obtained by reception of light to the computation section 10 (to be described later).

The first peripheral edge measurement mechanism 3 is fixed to a stage 22 for measurement movable in a radius direction of the rotation mechanism 2 as shown by a horizontal arrow in FIG. 4. The stage 22 for measurement is mounted on a linear guide 23 for measurement laid on the base 1. That is, the first peripheral edge measurement mechanism 3 has a configuration that when a pulse motor 24 for measurement is driven, the stage 22 for measurement moves in the radius direction of the movement mechanism 2. The stage 22 for measurement is provided with a light source 25 emitting light toward the peripheral edge of the wafer W.

The light source 25 is provided above the peripheral edge of the wafer W and the mirror 19 in order to facilitate detection of the position of the wafer W, and emits light toward the peripheral edge of the wafer W. More specifically, various parameters such as a wavelength band and a voltage of the light source 25 are inputted to the controller 41 through an operation section 40 such that the light to be emitted from the light source 25 has a predetermined wavelength and a predetermined intensity in accordance with a type of a protective sheet P to be joined to the top face of the wafer W. Then, based on the inputted parameters, the controller 41 controls the voltage and the wavelength band of the light source 25. In the embodiment of the present invention, a fluorescent tube outputting white light having a wavelength in a range from 300 to 800 nm is used as the light source 25. It is to be noted that the light source 25 corresponds to a first light source in the present invention.

Examples of the type of the protective tape P include a material and a color of a substrate, a surface processing status of the substrate, a thickness of the protective sheet P, and the like.

As illustrated in FIGS. 3 and 4, the second peripheral edge measurement mechanism 36 includes an optical camera 36A provided above the peripheral edge of the wafer W in a vertically movable manner, and an illumination device 36B emitting light toward the top face of the wafer W. In the illumination device 36B, a light emission angle is adjustable. It is to be noted that the optical camera 36A corresponds to second detection means and image capturing means in the present invention and the illumination device 36B corresponds to a second light source in the present invention.

The computation section 10 obtains a center of the wafer W by a computation and, also, obtains the position of the "V"-shaped notch K formed on the peripheral edge of the wafer W by a computation. Results of these computations are converted to digital signals. Then, the digital signals are sent to the rotation mechanism 2 and the respective pulse motors; thus, the handling position of the wafer W is determined.

Figure 5:
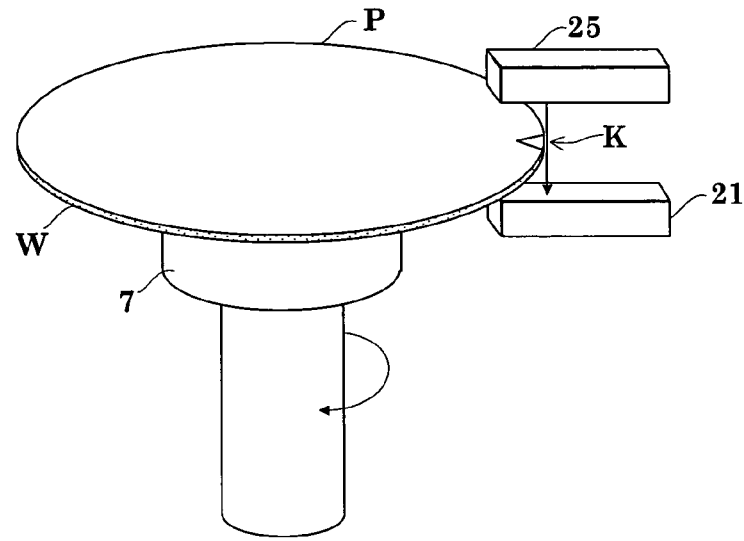
FIG. 5 illustrates an operation for rotating a semiconductor wafer.

The center of the wafer W is obtained as follows. As illustrated in FIG. 5, first, coordinates of the peripheral edge of the wafer W is obtained as positional information from a voltage generated when the light receiving sensor 21 linearly receives light emitted from the light source 25 to the peripheral edge of the wafer W while the holding stage 7 is allowed to rotate. Next, a point is optionally determined on a plane of the wafer W and, then, a plurality of distances between the peripheral edge and the optional point are calculated. Decentralization of a collection of distance data as results of the aforementioned calculations at a predetermined ratio is obtained by a computation in decreasing order of size; thus, the center of the wafer W is obtained. The center of the wafer W may be determined by a least square method and the like in addition to the aforementioned method.

In the computation section 10, actual image data of the peripheral edge of the wafer W, acquired by the optical camera 36A, is subjected to, for example, segmentation, so that a shape of an outer peripheral end is recognized. Thus, the position of the "V"-shaped notch K is identified based on a change in the outer peripheral end. Thereafter, actual image data of the "V"-shaped notch K is acquired. Thus, the position of the "V"-shaped notch K is calculated by pattern matching between the actual image data and reference image data. Herein, the reference image data is previously stored in a storage section 37 and is acquired from a reference wafer W which is equal to the wafer W to be measured. The pattern matching is performed by, for example, segmentation or normalized correlation search. Herein, the position of the "V"-shaped notch K is calculated as follows in this embodiment. That is, the position of the "V"-shaped notch K is obtained by center coordinates of the wafer W.

Figure 6:
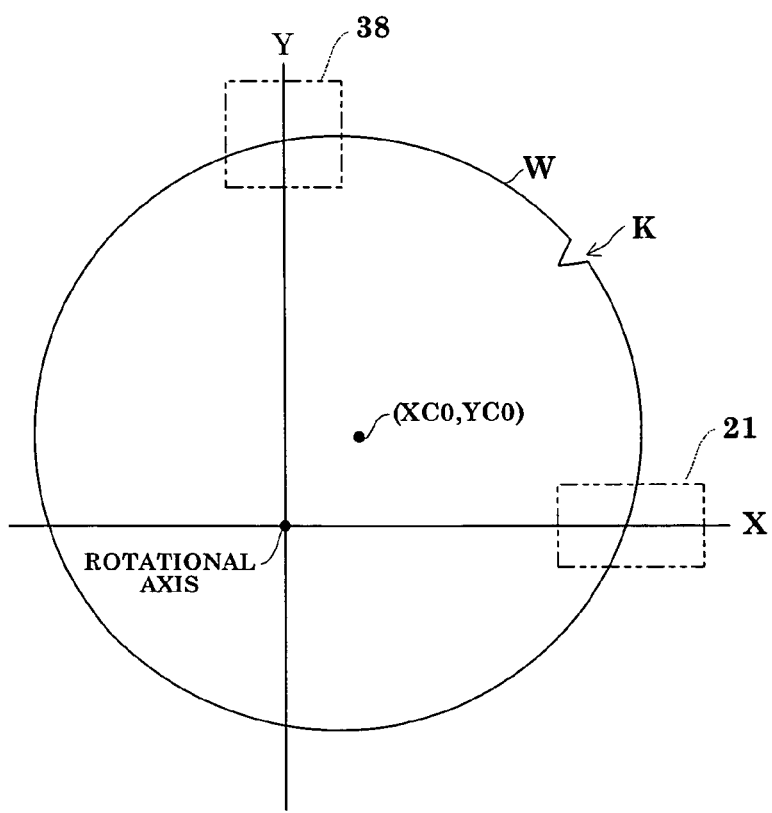
FIG. 6 schematically illustrates a status of a semiconductor wafer upon performance of a computing process.

First, the optical camera 36A captures images of the peripheral edge of the wafer W at regular pulse intervals during one rotational scanning of the holding stage 7; thus, actual image data is acquired. Herein, a digital signal indicative of a rotational angle sent from the pulse motor 9 for rotation is stored in the controller 41 while being correlated with actual image data. The actual image data acquired as described above is subjected to segmentation in order to identify a change at the "V"-shaped notch K; thus, actual image data of the "V"-shaped notch K is identified. Then, a position of the "V"-shaped notch K at a current point in time is obtained from a digital signal sent from the pulse motor 9 for rotation at a point in time when the identified image data is acquired. As a result, if the "V"-shaped notch K is located at a position illustrated in FIG. 6, a deviation amount from the position of the actual image data of the "V"-shaped notch K to the image capturing position is calculated in response to the reference position data of the optical camera 36A. In other words, as shown by a chain line in FIG. 7, the holding stage 7 is allowed to rotate so as to reach the image capturing position such that the "V"-shaped notch K comes in a field 38 of the optical camera 36A.

Herein, the actual image data of the peripheral edge of the wafer W is acquired again. Then, pattern matching between the actual image data and the reference image data stored in the storage section 37 is performed; thus, coordinates of a current position of the "V"-shaped notch K is obtained. Herein, as illustrated in FIG. 8, there is calculated a deviation amount in a case that the position of the "V"-shaped notch K shifts rightward with respect to a vertical center axis Y of the field 38 of the optical camera 36A.

Figure 8:
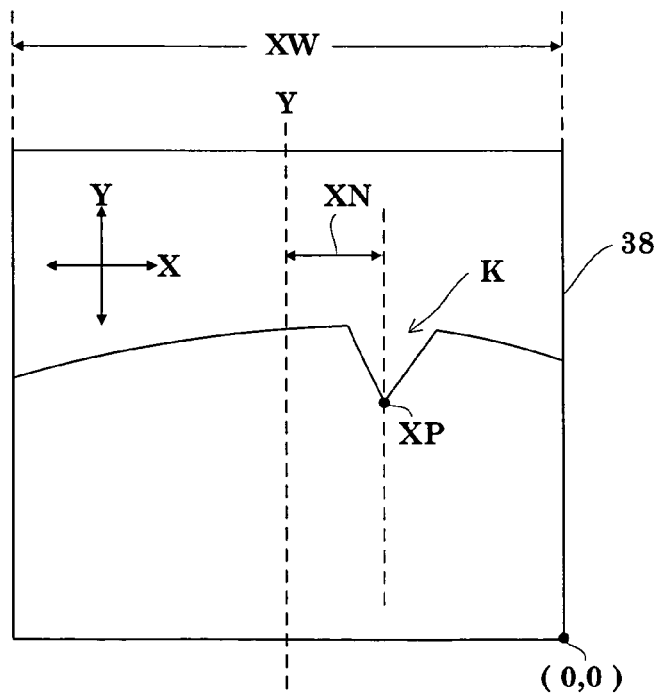
FIG. 8 illustrates a filed image of an optical camera.

As illustrated in FIG. 8, For example, if a lower right corner of the field 38 of the optical camera 36A is set at reference coordinates (0, 0), a field width in the X-axis direction is XW and a tapered-end of the "V"-shaped notch K is located at XP as a result of the pattern matching, a deviation amount XN from a field center Y(XW/2) on the X-axis is expressed by the following equation (1).

$$XN=(XW/2-XP) \times (\text{pixel size in X direction}) \tag{1}$$

In this case, a Y-axis coordinate is almost equal to a radius of a wafer W. Therefore, it is assumed herein that the deviation amount falls in an allowable range.

Figure 7:
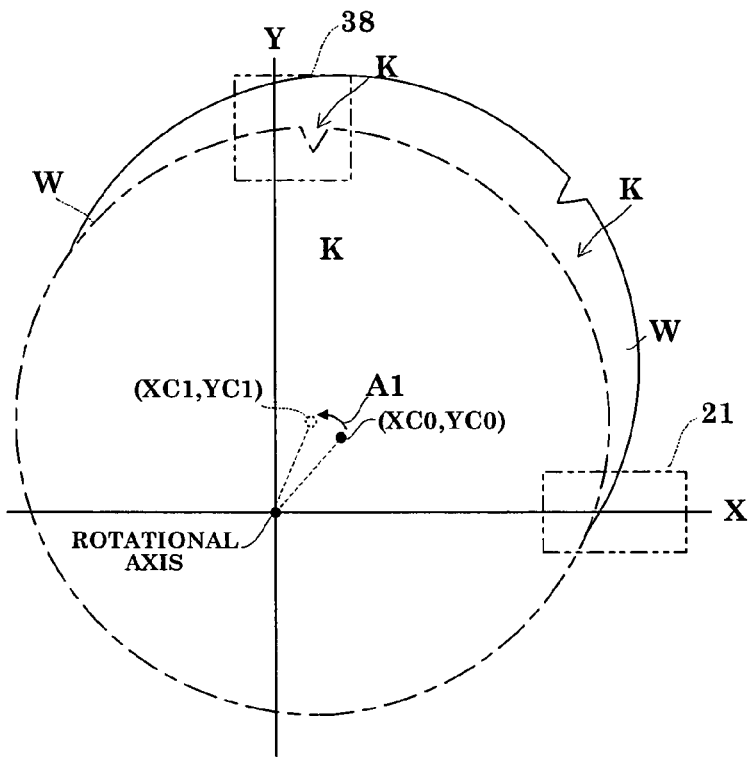
FIG. 7 schematically illustrates a status of a semiconductor wafer upon performance of a computing process.

Herein, as illustrated in FIG. 7, the center of the wafer W rotates leftward only by a rotational angle A1; therefore, center coordinates (XC1, YC1) after the rotation are obtained by the following equations (2) and (3).

$$XC1=XC0 \times \cos(A1) - YC0 \times \sin(A1) \tag{2}$$

$$YC1=XC0 \times \sin(A1) + YC0 \times \cos(A1) \tag{3}$$

The rotational angle A1 is obtained from a pulse count for each timing that an image of the "V"-shaped notch K is captured.

Next, there is obtained a rotational angle AN of coordinates (XN, YN) on the "V"-shaped notch K when viewed from the center coordinates (XC1, YC1) after the rotation. If a radius of the wafer W is WR, the rotational angle AN is obtained by the following equation (4).

$$AN=a\tan((YN-YC1)/(XN-XC1))=a\tan((WR-YC1)/(XN-XC1)) \tag{4}$$

Next, a rotational angle AD as a correction amount for correcting the position of the "V"-shaped notch K is obtained by the following equation (5).

$$AD=-AN+(\text{offset angle}) \tag{5}$$

Herein, the offset angle corresponds to rotation of the holding stage 7 at a distance longer by one rotation upon performance of alignment in order to stop the rotational scanning slowly.

Next, a rotation pulse count TP for correction is obtained by the following equation (6).

$$TP=AD/(\text{rotational angle per one pulse}) \tag{6}$$

The position of the "V"-shaped notch K requires a rotational angle AD corresponding to an offset amount after the rotation by the rotational angle AN. Therefore, a rotational angle A required herein is expressed as follows: AN+AD. Corrected center coordinates (XD, YD) of the wafer W after the rotation are obtained by the following equations (7) and (8).

$$XD=XC0 \times \cos(A) - YC0 \times \sin(A) \tag{7}$$

$$YD=XC0 \times \sin(A) + YC0 \times \cos(A) \tag{8}$$

Herein, the coordinates (XC0, YC0) are the center coordinates obtained initially through a computation by a transmission scheme.

In order to correct the center position and the deviation amounts of the "V"-shaped notch K in the X-axis and Y-axis directions, each obtained as described above, a pulse count XP for driving the X-axis pulse motor 15 is obtained from an equation: XP=−XD/movement amount per one pulse, and a pulse count XP for driving the Y-axis pulse motor 17 is obtained from an equation: YP=−YD/movement amount per one pulse.

The controller 41 outputs the obtained pulse counts XP and YP to the X-axis pulse motor 15 and the Y-axis pulse motor 16, respectively. Thus, a movement amount for position correction is obtained.

Figure 9:
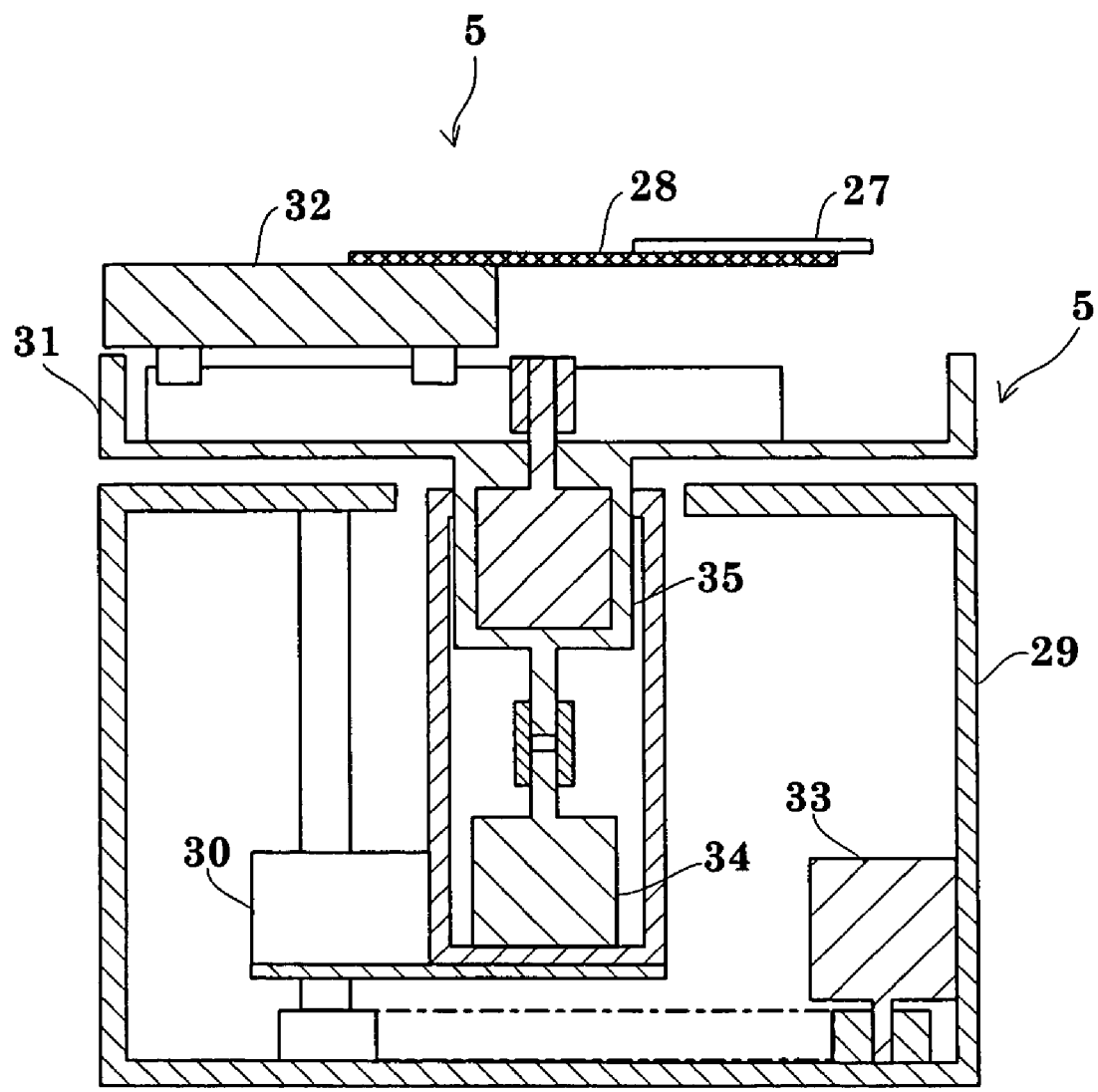
FIG. 9 is a side view schematically illustrating a configuration of a transport mechanism.

Next, as illustrated in FIG. 9, the transport mechanism 5 includes a robot arm 27 and an arm movement table 28. Herein, the robot arm 27 has a suction groove 26 for suction-holding a surface of the protective sheet P joined to the top face, having the circuit pattern formed thereon, of the wafer W upon transport of the wafer W, and is formed into a horse shoe shape. The arm movement table 28 allows the robot arm 27 to move in vertical and horizontal directions.

The arm movement table 28 includes a Z-axis stage 30 attached to a transporter base 29 so as to freely move in a vertical direction, a θ-axis stage 31 attached to the Z-axis stage 30 so as to freely rotate, and an R-axis stage 32 attached to the θ-axis stage 31 so as to freely advance in a radius direction of the θ-axis stage 31. Herein, the Z-axis stage 30 is movable/rotatable when a Z-axis pulse motor 33 fixedly mounted on the transporter base 29 is driven. The θ-axis stage 31 is movable/rotatable when a θ-axis pulse motor 34 fixedly mounted on the Z-axis stage 30 is driven. The R-axis stage 32 is movable/rotatable when an R-axis pulse motor 35 fixedly mounted on the θ-axis stage 31 is driven.

The aforementioned pulse motors are connected to the controller 41 in order to control rotation/movement of the holding stage 7, the X-axis stage 12, the Y-axis stage 13, the stage 22 for measurement, and the robot arm 27. The controller 41 has the computation section 10 connected thereto in order to control each pulse motor based on a result of a computation by the light receiving sensor 21.

Figure 10:
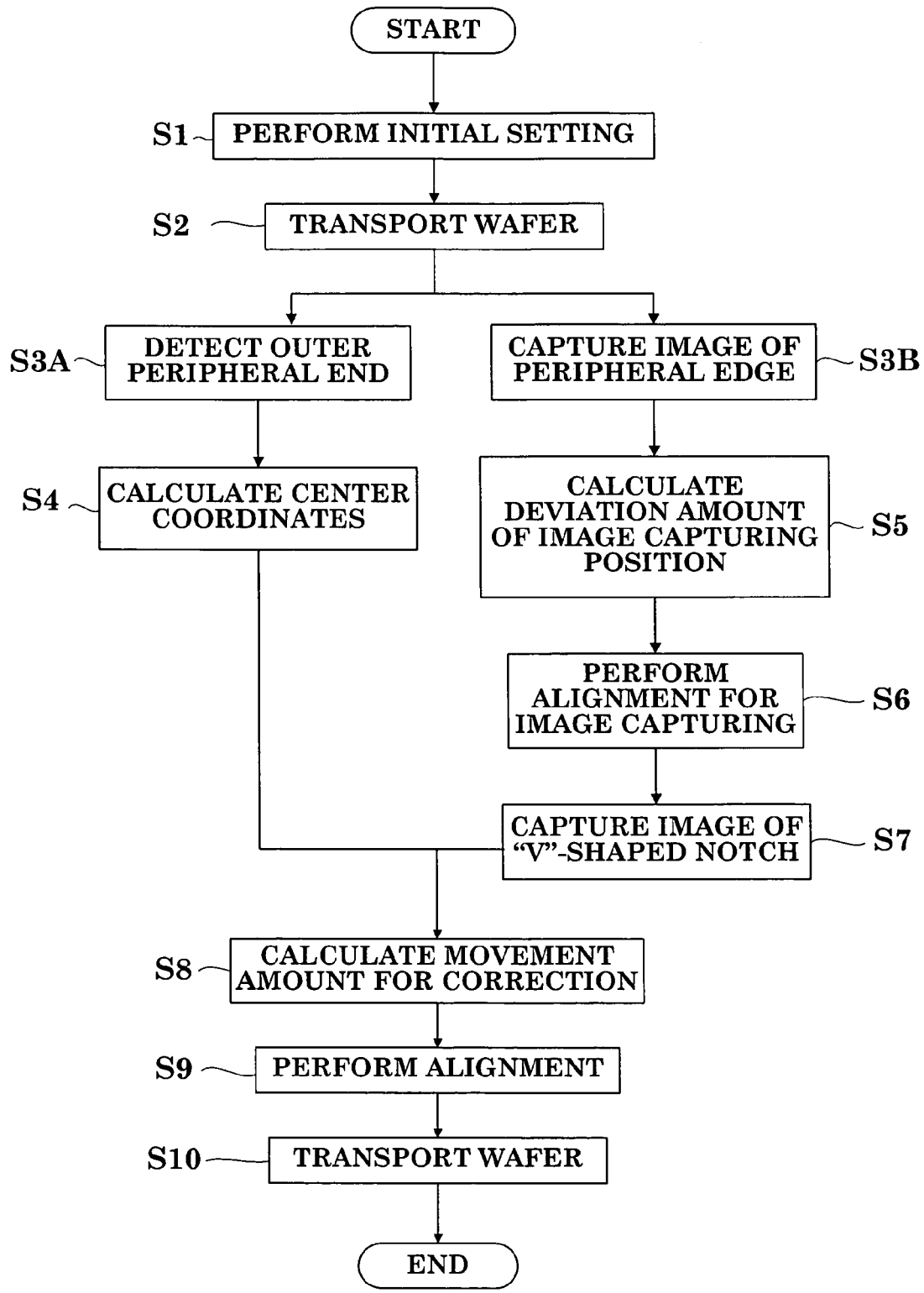
FIG. 10 is a flowchart showing processes in the apparatus according to the embodiment of the present invention.

Next, description will be given of a sequence of operations for adjusting the handling position of the wafer W by means of the apparatus according to the embodiment of the present invention with reference to a flowchart shown in FIG. 10.

First, initial parameters required for alignment of the wafer W are inputted to the controller 41 through the operation section 40. Examples of the initial parameters include a diameter of the wafer W, a material for a substrate of the protective sheet P, a total thickness of the protective sheet P, a color of the substrate, a material and a thickness of a coating film, timing at which the optical camera 36A captures an image, and the like. Upon completion of the initial setting, when each pulse motor is driven, the rotation mechanism 2, the first peripheral edge measurement mechanism 3 and the vertical drive mechanism 4 are actuated; thus, a scanning start position is adjusted (step S1).

Upon completion of the adjustment of the scanning start position, each of stacked wafers W horizontally contained in a cassette (not illustrated) at regular intervals is suction-held by the robot arm 27 of the transport mechanism 5 and, then, is placed on the holding stage 7 of the apparatus according to the embodiment of the present invention (step S2).

The wafer W placed on and suction-held by the holding stage 7 is subjected to scanning including an offset amount substantially once while rotating about a center axis of the holding stage 7. Concurrently, the light source 25 emits light toward a peripheral edge of the wafer W, and the light receiving sensor 21 linearly sends data of light reception voltage to the computation section 10 (step S3A).

After completion of the rotation scanning, the computation section 10 obtains center coordinates of the wafer W from the acquired light reception voltage (step S4).

In a state that the illumination device 36B located diagonally above the wafer W irradiates the peripheral edge of the wafer W with light when the rotation scanning is performed, the optical camera 36A captures images of the peripheral edge of the wafer W at regular time intervals; thus, actual image data is acquired (step S3B).

After completion of the rotation scanning, the computation section 10 recognizes an outer peripheral end of the wafer W based on the acquired actual image data, identifies actual image data with a variation, that is, actual image data of the "V"-shaped notch K, and obtains a deviation amount (a pulse count) between a digital signal correlated with the actual image data and sent from the pulse motor 9 for rotation and an image capturing position of the optical camera 36A (step S5).

The controller 41 sends a digital signal converted to the obtained pulse count to the pulse motor 9 for rotation, so that the holding stage 7 is allowed to rotate such that the "V"-shaped notch K falls in the field of the optical cameral 36A (step S6).

After completion of the rotation of the holding stage 7, the optical camera 36A actuated by the controller 41 captures an image of the peripheral edge, that is, the "V"-shaped notch K of the wafer W; thus, actual image data is acquired (step S7).

Then, pattern matching between the actual image data and reference image data previously stored in the storage section 37 is performed; thus, coordinates of the "V"-shaped notch K are obtained. Thereafter, a movement amount for correcting the position of the "V"-shaped notch K to a reference position is calculated from the center coordinates of the wafer W obtained by the computation section 10 in step S4 and the aforementioned equations (step S8).

The controller 41 drives the X-axis pulse motor 15 and the Y-axis pulse motor 17 to thereby allow the X-axis stage 12 and the Y-axis stage 13 to move based on the obtained movement amount of the wafer W; thus, the center of the wafer W is aligned. Concurrently, the "V"-shaped notch K is aligned with the reference position by rotation of the holding stage 7 (step S9).

After completion of the alignment, the wafer W is suction-held by the robot arm 27 and, then, is transported from the holding stage 7 to the cassette (not illustrated) (step S10). Thus, a sequence of operations is finished.

As described above, the apparatus for determining a position of a semiconductor wafer according to the present invention provides the following advantages. That is, even when a coating film which is made of metal M and hinders transmission of light is formed by deposition on the rear face of the protective sheet P, the center of the wafer W and the position of the "V"-shaped notch K can be obtained with good accuracy. In other words, the coordinates of the peripheral edge of the wafer W can be obtained with good accuracy by a transmission scheme using the light source 25 and the light receiving sensor 21. Therefore, the center of the wafer W can be obtained with good accuracy. In addition, the detection site, that is, the position of the "V"-shaped notch K formed on the peripheral edge of the wafer W can be obtained with good accuracy from a variation amount of the reflection light from the optical camera 36A and the illumination device 36B.

Accordingly, it is possible to determine the handling position of the wafer W with good accuracy based on the center of the wafer W and the position of the "V"-shaped notch K.

The present invention is not limited to the aforementioned embodiment, and may be embodied as follows.

(1) In the aforementioned embodiment, as an example, the wafer W is coated with the coating film, which is made of metal and shields light, at the rear face of the protective sheet P bared at the "V"-shaped notch K. However, the present invention is not limited thereto. For example, the wafer W may be provided with a protective sheet P formed of a colored substrate in order to hinder transmission of light. Alternatively, the wafer W may be covered with an opaque glass or an opaque plate. The present invention is also applicable to a workpiece having a detection site covered with another member, in addition to the wafer W.

(2) In the aforementioned embodiment, as shown by a broken line in FIG. 3, a white body 39 such as a white sheet-shaped body or a white plate may be provided so as to be opposite to the optical camera 36A with the wafer W interposed therebetween. In this case, light emitted from the illumination device 36B toward the peripheral edge of the wafer W passes the peripheral edge of the wafer W and, then, is reflected by the white body 39. Therefore, in an image captured by the optical camera 36A, a portion corresponding to the peripheral edge of the wafer W is emphasized. Accordingly, it is possible to readily identify the position of the "V"-shaped notch K with improved accuracy.

(3) In the aforementioned embodiment, after one rotation scanning, the position of the "V"-shaped notch K is identified and, then, actual image data of the peripheral edge of the wafer W including the "V"-shaped notch K is acquired again. However, the position of the "V"-shaped notch K may be obtained by pattern matching between actual image data acquired by one rotation scanning and reference image data.

(4) In the aforementioned embodiment, the light source 25 and the illumination device 36B are provided separately. However, a single light source may be used in the present invention. In this case, it is preferable that an emission angle of light from the light source 25 is changeable such that the top face of the wafer W can be irradiated with the light from the light source 25.

The present invention may be embodied in other specific forms without departing from the spirit or essential attributes thereof and, accordingly, reference should be made to the appended claims, rather than to the foregoing specification, as indicating the scope of the invention.

What is claimed is:

1. A method for detecting a notch as a detection site for alignment formed on a peripheral edge of a semiconductor wafer having a protective sheet joined thereto, thereby determining a handling position of the semiconductor wafer, the method comprising:
    a first irradiation step of irradiating the peripheral edge of the semiconductor wafer having the protective sheet joined thereto with light from a light source;
    a light receiving step of detecting the light from the light source through first detection means provided so as to be opposite to the light source with the semiconductor wafer interposed therebetween in a state that the peripheral edge of the semiconductor wafer is irradiated with the light from the light source;
    a center determination step of
        subjecting, to coordinate transformation, the position of the light detected by the first detection means along the peripheral edge of the semiconductor wafer,
        calculating a distance between coordinates of a point determined on a plane of the semiconductor wafer and each coordinates of the peripheral edge of the semiconductor wafer, and
        determining center coordinates based on a variation amount of a collection of the obtained distance data;
    a second irradiation step of irradiating the peripheral edge of the semiconductor wafer with light from a light source;
    a reflection light detection step of detecting light reflected from the semiconductor wafer through second detection means in a state that the peripheral edge of the semiconductor wafer is irradiated with the light from the light source by relatively moving a pair of the light source and the first detection means and the semiconductor wafer in such a manner that the pair of the light source and the first detection means rotates about a center axis of the semiconductor wafer; and
    a detection site determination step of determining a position of the notch based on a variation in intensity of the reflection light detected by the second detection means.

2. The method of claim 1, wherein
a bottom face of the semiconductor wafer having the protective sheet joined thereto and a rear face of the protective sheet bared at the notch are coated with a coating film for hindering transmission of light.

3. The method of claim 2, wherein
the second detection means detects the reflection light in a state that one of a white sheet and a white plate is provided so as to be opposite to the light source with the semiconductor wafer interposed therebetween.

4. The method of claim 3, wherein
the light source is a light source different from the light source provided so as to be opposite to the first detection means, is disposed on a side of the second detection means, and changes an angle of the light to be emitted to the semiconductor wafer.

5. A method for detecting a notch as a detection site for alignment formed on a peripheral edge of a semiconductor wafer having a protective sheet joined thereto, thereby determining a handling position of the semiconductor wafer, the method comprising:
    a first irradiation step of irradiating the peripheral edge of the semiconductor wafer having the protective sheet joined thereto with light from a light source;
    a light receiving step of detecting the light from the light source through first detection means provided so as to be opposite to the light source with the semiconductor wafer interposed therebetween in a state that the peripheral edge of the semiconductor wafer is irradiated with the light from the light source;
    a center determination step of
        subjecting, to coordinate transformation, the position of the light detected by the first detection means along the peripheral edge of the semiconductor wafer,
        calculating a distance between coordinates of a point determined on a plane of the semiconductor wafer and each coordinates of the peripheral edge of the semiconductor wafer, and
        determining center coordinates based on a variation amount of a collection of the obtained distance data;
    a second irradiation step of irradiating the peripheral edge of the semiconductor wafer with light from a light source;
    a reflection light detection step of detecting light reflected from the semiconductor wafer through an image capturing means in a state that the peripheral edge of the semiconductor wafer is irradiated with the light from an image capturing means by relatively moving a pair of the light source and the first detection means and the semiconductor wafer in such a manner that the pair of the light source and the first detection means rotates about a center axis of the semiconductor wafer; and
    a detection site determination step of
        capturing, through the image capturing means, an image of the peripheral edge of the semiconductor wafer irradiated with the light from the light source, and
        comparing predetermined reference image data of the notch with actual image data obtained by the image capturing means, thereby determining a position of the notch formed on the peripheral edge of the semiconductor wafer.

6. The method of claim 5, wherein
the position of the notch is determined by pattern matching between the reference image data and the actual image data.

7. The method of claim 5, wherein
a bottom face of the semiconductor wafer having the protective sheet joined thereto and a rear face of the protective sheet bared at the notch are coated with a coating film for hindering transmission of light.

8. The method of claim 7, wherein
the second detection means detects the reflection light in a state that one of a white sheet and a white plate is provided so as to be opposite to the light source with the semiconductor wafer interposed therebetween.

9. The method of claim 8, wherein
the light source is a light source different from the light source provided so as to be opposite to the first detection means, is disposed on a side of the second detection means, and changes an angle of the light to be emitted to the semiconductor wafer.

10. An apparatus for detecting a notch as a detection site for alignment formed on a peripheral edge of a semiconductor wafer having a protective sheet joined thereto, thereby determining a handling position of the semiconductor wafer, the apparatus comprising:
holding means for holding the semiconductor wafer having the protective sheet joined thereto;
a light source for irradiating, with light, the peripheral edge of the semiconductor wafer held by the holding means;
first detection means, provided so as to be opposite to the light source with the semiconductor wafer interposed therebetween, for detecting a position of the light emitted from the light source;
rotational movement means for allowing a pair of the light source and the first detection means and the holding means to move relatively in such a manner that the pair of the light source and the first detection means moves along the peripheral edge of the semiconductor wafer held by the holding means;
second detection means for detecting light reflected from the semiconductor wafer among the light emitted from the light source toward the peripheral edge of the semiconductor wafer;
computation means for
subjecting, to coordinate transformation, the position of the light in a state that the rotational movement means allows a pair of the light source and light receiving means and the holding means to move relatively,
calculating a distance between coordinates of a point determined on a plane of the semiconductor wafer and each coordinates of the peripheral edge of the semiconductor wafer,
determining center coordinates based on a variation amount of a collection of the obtained distance data, and
obtaining a position of the notch based on a variation in intensity of the reflection light detected by the second detection means; and
control means for controlling the rotational movement means so as to perform alignment of the handling position of the semiconductor wafer held by the holding means in accordance with a result of the computations by the computation means.

11. The apparatus of claim 10, wherein
the light source includes:
a first light source provided so as to be opposite to the first detection means with the semiconductor wafer interposed therebetween; and
a second light source for irradiating the peripheral edge of the semiconductor wafer with light.

12. The apparatus of claim 11, wherein
the second light source changes an angle of the light to be emitted to the peripheral edge of the semiconductor wafer.

13. The apparatus of claim 12, further comprising:
one of a white sheet and a white plate provided so as to be opposite to the second light source with the semiconductor wafer interposed therebetween.

14. An apparatus for detecting a notch as a detection site for alignment formed on a peripheral edge of a semiconductor wafer having a protective sheet joined thereto, thereby determining a handling position of the semiconductor wafer, the apparatus comprising:
holding means for holding the semiconductor wafer having the protective sheet joined thereto;
a light source for irradiating, with light, the peripheral edge of the semiconductor wafer held by the holding means;
first detection means, provided so as to be opposite to the light source with the semiconductor wafer interposed therebetween, for detecting a position of the light emitted from the light source;
rotational movement means for allowing a pair of the light source and the first detection means and the holding means to move relatively in such a manner that the pair of the light source and the first detection means moves along the peripheral edge of the semiconductor wafer held by the holding means;
an image capturing means for detecting light reflected from the semiconductor wafer among the light emitted from the light source toward the peripheral edge of the semiconductor wafer;
computation means of
subjecting, to coordinate transformation, the position of the light in a state that the rotational movement means allows a pair of the light source and light receiving means and the holding means to move relatively,
calculating a distance between coordinates of a point determined on a plane of the semiconductor wafer and each coordinates of the peripheral edge of the semiconductor wafer,
determining center coordinates based on a variation amount of a collection of the obtained distance data, and
capturing, through the image capturing means, an image of the peripheral edge of the semiconductor wafer irradiated with the light from the light source, and
comparing predetermined reference image data of the notch with actual image data obtained by the image capturing means, thereby determining a position of the notch formed on the peripheral edge of the semiconductor wafer; and
control means for controlling the rotational movement means so as to perform alignment of the handling position of the semiconductor wafer held by the holding means in accordance with a result of the computations by the computation means.

15. The apparatus of claim 14, wherein
the computation means determines the position of the notch by pattern matching between the reference image data and the actual image data.

16. The apparatus of claim 14, wherein
the light source includes:
a first light source provided so as to be opposite to the first detection means with the semiconductor wafer interposed therebetween; and
a second light source for irradiating the peripheral edge of the semiconductor wafer with light.

17. The apparatus of claim 16, wherein
the second light source changes an angle of the light to be emitted to the peripheral edge of the semiconductor wafer.

18. The apparatus of claim 17, further comprising:
one of a white sheet and a white plate provided so as to be opposite to the second light source with the semiconductor wafer interposed therebetween.

* * * * *